US012708597B2

(12) United States Patent
Barfoot et al.

(10) Patent No.: US 12,708,597 B2
(45) Date of Patent: Aug. 18, 2026

(54) HAIR CONDITIONING COMPOSITION FOR IMPROVED DEPOSITION

(71) Applicant: Conopco, Inc., Englewood Cliffs, NJ (US)

(72) Inventors: Richard Jonathan Barfoot, Chesterfield (GB); Cesar Ernesto Mendoza Fernandez, Liverpool (GB); Amelie Laura Simon, Liverpool (GB)

(73) Assignee: Conopco, Inc., Englewood Cliffs, NJ (US)

(*) Notice: Subject to any disclaimer, the term of this patent is extended or adjusted under 35 U.S.C. 154(b) by 271 days.

(21) Appl. No.: 18/258,030

(22) PCT Filed: Dec. 1, 2021

(86) PCT No.: PCT/EP2021/083831

§ 371 (c)(1),
(2) Date: Jun. 16, 2023

(87) PCT Pub. No.: WO2022/135858

PCT Pub. Date: Jun. 30, 2022

(65) Prior Publication Data

US 2024/0082130 A1 Mar. 14, 2024

(30) Foreign Application Priority Data

Dec. 21, 2020 (EP) .................................... 20216225

(51) Int. Cl.

| | |
|---|---|
| ***A61K 8/44*** | (2006.01) |
| ***A61K 8/73*** | (2006.01) |
| ***A61K 8/891*** | (2006.01) |
| ***A61K 8/892*** | (2006.01) |
| ***A61K 8/898*** | (2006.01) |
| ***A61Q 5/12*** | (2006.01) |

(52) U.S. Cl.

CPC ................ *A61K 8/44* (2013.01); *A61K 8/731* (2013.01); *A61K 8/891* (2013.01); *A61K 8/892* (2013.01); *A61K 8/898* (2013.01); *A61Q 5/12* (2013.01)

(58) Field of Classification Search

CPC .......... A61K 8/44; A61K 8/731; A61K 8/891; A61K 8/892; A61K 8/898; A61K 8/342; A61K 8/416; A61Q 5/12

See application file for complete search history.

(56) References Cited

U.S. PATENT DOCUMENTS

| | | | |
|---|---|---|---|
| 5,374,421 | A | 12/1994 | Tashiro et al. |
| 2001/0012823 | A1 | 8/2001 | Giles |
| 2004/0115155 | A1 | 6/2004 | Salvador et al. |
| 2005/0020468 | A1 | 1/2005 | Frantz et al. |
| 2005/0175569 | A1 | 8/2005 | Fack |
| 2008/0292575 | A1 | 11/2008 | Uehara |
| 2013/0259817 | A1 | 10/2013 | Uehara et al. |

FOREIGN PATENT DOCUMENTS

| | | | | |
|---|---|---|---|---|
| CN | 1832720 A | 9/2006 | | |
| CN | 101677927 A | 3/2010 | | |
| CN | 105492588 A | 4/2016 | | |
| DE | 3527974 A1 * | 2/1987 | .............. | A61Q 5/06 |
| EP | 0530974 | 3/1993 | | |
| GB | 2316615 | 3/1998 | | |
| JP | 8198828 A2 | 8/1996 | | |
| JP | 2005060271 | 3/2005 | | |
| WO | WO9962492 | 12/1999 | | |
| WO | WO0143718 | 6/2001 | | |
| WO | WO02102334 | 12/2002 | | |

(Continued)

OTHER PUBLICATIONS

"STD1569 Public Report" National Industrial Chemicals Notification and Assessment Scheme (NICNAS). Available online Dec. 2015. https://www.industrialchemicals.gov.au/sites/default/files/STD1569%20Public%20Report%20PDF.pdf. Accessed Jul. 10, 2025. (Year: 2015).*

(Continued)

*Primary Examiner* — Robert A Wax
(74) *Attorney, Agent, or Firm* — Carter, DeLuca & Farrell, LLP; George Likourezos; Bret P. Shapiro

(57) ABSTRACT

A composition comprising: •(i) 0.01 to 10 wt % of a branched cationic conditioning surfactant selected from structure 1•wherein: ••$R_1$ and $R_2$ comprise linear alkyl chains, saturated or unsaturated, with carbon-carbon chain lengths of from $C_4$ to $C_{20}$; ••$R_3$ comprise either a proton or linear or branched alkyl chains, saturated or unsaturated, with carbon-carbon chain lengths of from $C_1$ to $C_5$; ••n has a range of from 0 to 10; ••$X^G$ is an organic or inorganic anion; •(ii) 0.1 to 10 wt % of a linear fatty material having at least one linear carbon-carbon chain, selected from a linear fatty alcohol, a linear alkoxylated fatty alcohol, a linear fatty acid and mixtures thereof; •(iii) 0.1 to 5 wt % of a nonionic structurant; and •(iv) a particulate benefit agent selected from conditioning actives; wherein the molar ratio of branched cationic surfactants (i) to linear fatty material (ii) is in the range of from 1:20 to 1:1, results in improved particulate benefit agent deposition onto bleached hair. A preferred structurant is hydroxyethyl cellulose and preferred conditioning actives are silicone emulsions.

15 Claims, No Drawings

(56) References Cited

FOREIGN PATENT DOCUMENTS

| | | | |
|---|---|---|---|
| WO | 2015031418 A1 | 3/2015 |
| WO | WO2017172117 | 10/2017 |
| WO | WO2020061658 | 4/2020 |
| WO | WO2020126377 | 6/2020 |
| WO | WO2020126659 | 6/2020 |
| WO | WO2020126660 | 6/2020 |
| WO | WO2020127542 | 6/2020 |

OTHER PUBLICATIONS

Machine translation of DE-3527974-A1 (Konrad, E.) Feb. 12, 1987; obtained from Google Translate on Jul. 10, 2025. (Year: 1987).*

Anonymous; Structure XL (28-030A) Hydroxypropyl starch phosphate; Internet Citation—Personal Care Product Overview; Jun. 17, 2002; pp. 1-2, Retrieved from Internet: URL:http://www.personalcarepolymers.com/site/prodview.asp?id=028030A, XP002376850; .; National Starch & Chemical Company.

Search Report and Written Opinion EP20216206; Jun. 29, 2021; European Patent Office (EPO).

Search Report and Written Opinion in EP20216225; Jun. 29, 2021; European Patent Office (EPO).

Search Report and Written Opinion in EP20216189; Jun. 29, 2021; European Patent Office (EPO).

Search Report and Written Opinion in EP20216222; Jun. 30, 2021; European Patent Office (EPO).

Search Report and Written Opinion in PCTEP2021084067; Mar. 18, 2022; World Intellectual Property Org. (WIPO).

Search Report and Written Opinion in PCTEP2021084387; Mar. 18, 2022; World Intellectual Property Org. (WIPO).

Search Report and Written Opinion in PCTEP2021084356; Mar. 18, 2022; World Intellectual Property Org. (WIPO).

Search Report and Written Opinion in PCTEP2021083831; Mar. 28, 2023; World Intellectual Property Org. (WIPO).

Chemspider, "Dioleoylisopropyl Dimonium Methosulfate", Royal Society of Chemistry (2 pages). Available at: CSID:52084537, https://www.chemspider.com/Chemical-Structure.52084537.html, (last accessed Mar. 11, 2026).

* cited by examiner

HAIR CONDITIONING COMPOSITION FOR IMPROVED DEPOSITION

CROSS-REFERENCE TO RELATED APPLICATIONS

This application is a U.S. national phase application under 35 U.S.C. § 371 of International Application No. PCT/EP2021/083831, filed on Dec. 1, 2021, which claims priority to European Patent Application No. 20216225.1, filed Dec. 21, 2020, the entire disclosures of which are incorporated herein by reference in their entireties, for any and all purposes.

FIELD OF THE INVENTION

The invention is concerned with conditioning compositions, comprising a branched cationic surfactant in combination with fatty alcohol and a structurant, for the treatment of bleached hair, which comprise a benefit agent to be deposited onto the hair during use and particularly relates to a conditioning composition that enables increased amounts of benefit agent to be deposited to bleached hair.

BACKGROUND AND PRIOR ART

In personal care compositions, such as hair treatment compositions, the deposition and delivery of benefit agents are often key drivers of product performance. For example, many of the hair conditioner products in the market today work to deliver benefits to hair by depositing benefit agents such as fragrance materials, silicones and damage repair actives onto the hair during wash and care processes.

However, consumers report being disappointed by the level of benefit derived from use of some compositions. This is usually caused by insufficient amount of benefit agents being delivered to the surface. It is, therefore, desirable to develop compositions that provide improved delivery of benefit materials to a surface, for example hair.

Bleached hair is known to be particularly poor at retaining silicones during and after application, leading to low levels of deposition and inadequate benefit to the user. The user, therefore, has to apply more product and may never reach the level of conditioning that is desired. Indeed, we have found that measured silicone levels delivered to bleached hair can be less than 20% than that achieved for the same product used on virgin hair.

Various types of branched cationic compounds are known in hair treatment compositions for a variety of benefits.

WO 17/172117 discloses a composition for treating keratinous substrates comprising a cationic agent comprising a defined first quaternary ammonium compound and an imidazoline compound, a modified starch, two silane compounds, a cationic vinylpyrrolidone polymer and water. Hair treated with the compositions is purported to have improved mass, body, volume, to be easily rinsed, to dry fast, to stay clean longer and be sufficiently conditioned. US 2005/175569 discloses cosmetic compositions, for example for conditioning and styling hair, comprising a cationic surfactant, which may be a quaternary ammonium salt.

JP 2005-060271 discloses an aqueous hair cosmetic composition that can comprise (A) a dimethylpolysiloxane represented by general formula (1), (B) a dimethylpolysiloxane represented by general formula (2), (C) a cyclic dimethylpolysiloxane represented by general formula (3) at a ratio of [(B)+(C)]/(A) greater than or equal to 1; and (D) an additional quaternary ammonium component. The composition is said to provide a range of conditioning benefits to hair in the wet, rinse and dry stages.

Our own published applications WO 02/102334 and WO 01/43718 provide aqueous hair treatment compositions having cleansing and conditioning properties that comprise quaternary ammonium based cationic surfactants having defined hydrocarbyl chains.

WO 2020/126377 A1 (UNILEVER) discloses compositions for improved deposition of benefit agents to hair. An example discloses a composition comprising (i) behentrimonoum chloride, (ii) cetearyl alcohol, (iii) an emulsified silicone and (iv) N,N,N-trimethyl-2-((2-octyldodecyl)oxy)-2-oxoethan-1-aminium methanesulphonate.

WO 2020/061658 A1 (L'OREAL) discloses compositions for the provision of styling benefits to hair, such as anti-frizz properties, volume control, and conditioning. The hair treatment compositions include: (a) a cationic surfactant that is an esterquat; (b) a cationic surfactant that is not an esterquat; (c) a silicone oil; (d) a fatty alcohol; (e) water; and (f) optionally, one or more of: (i) a nonionic polymer; (ii) a cationic polymer; and (iii) an amino silicone.

WO 99/62492 A1 (PROCTER & GAMBLE) discloses a conditioning composition comprising (1) at least 3% of a compound having a melting point of at least 25° C.; (2) an emulsifying agent selected from the group consisting of amines, betaines, nonionic compounds, and mixtures thereof; (3) a quaternary compound; and (4) an aqueous carrier; wherein the composition shows a DSC profile having substantially no peaks larger than about 3 mJ/mg from about 40° C. to 65° C.

GB 2 316 615 A (R & C PRODUCTS PTY LTD) discloses compositions for improved conditioning benefits comprising: i) 0.1 to 10% C18-C22 alkyl quaternary ammonium, e.g. behentrimonium chloride, ii) 0.1 to 10% C12-C22 dialkyl quaternary ammonium, e.g. dicetyldimonium chloride, iii) 0.01 to 5% non-volatile polyalkyl silicone, e.g. dimethyl silicone, iv) 0.01 to 5% non-volatile polyalkyl hydroxy terminated silicone, e.g. dimethiconol, v) 0.01 to 5% emulsified cationic amino functional silicone, e.g. amodimethicone, vi) 0.1 to 10% long chain fatty alcohol, e.g. cetyl alcohol vii) balance water.

U.S. Pat. No. 5,374,421 A (TASHIRO KAZUHIRO) discloses a composition for hair treatment containing (a) 0.1-10 wt. % of a modified silicone polymer having at least one alkoxy group and a melting point of not lower than 30° C., (b) 0.1-20 wt. % of a cationic surface active agent, (c) 0.1-30 wt. % of an oily or fatty material, (d) 0.1-90 wt. % of an organic liquid which is compatible with water and has at least one hydroxy group, and (e) water.

WO 2020/126659 A1 (UNILEVER PLC) discloses a composition for improved benefit agent deposition onto hair, comprising: (i) 0.01 to 10 wt % of a linear, cationic conditioning surfactant; (ii) 0.1 to 10 wt % of a linear fatty material; (iii) a particulate benefit agent; (iv) 0.01 to 5 wt %, at 100% active, of a branched cationic co-surfactant, as defined by a structure (1); wherein the molar ratios of branched cationic co-surfactants (iv) to linear cationic surfactants (i) are in the range of from 1:20 to 1:1; the compositions having a viscosity of 5,000 to 750,000 cp.

WO 2020/127542 A1 (UNILEVER PLC) discloses a composition comprising: a) a conditioning base comprising: i) a cationic conditioning surfactant having from 16 to 32 carbon atoms; ii) a fatty alcohol having from 8 to 22 carbon atoms; and b) from 0.1 to 10 wt % of a conditioning silicone; (c) from 0.1 to 5 wt % of a diesterquat selected from a diesterquat that comprises branched, saturated chains, a diesterquat that comprises unbranched, unsaturated chains, and mixtures thereof; wherein the ratio of b) to c) is from 1:1 to 1:0.1, to provide improved deposition of silicone on hair surfaces.

WO 2020/126660 A1 (UNILEVER PLC) discloses a composition comprising: (i) 0.01 to 10 wt % of a linear, cationic conditioning surfactant; (ii) 0.1 to 10 wt % of a linear fatty material; (iii) a particulate benefit agent selected from conditioning actives, scalp actives, encapsulated fragrance, emulsified fragrance, and mixtures thereof; (iv) 0.01 to 5 wt %, at 100% active, of a branched cationic co-surfactant, selected from structure 1, structure 2, structure 3 and mixtures thereof; wherein the molar ratios of branched cationic co-surfactants (iv) to linear cationic surfactants (i) are in the range of from 1:20 to 1:1 to provide improved particulate benefit agent deposition onto hair.

Whilst branched materials are known in home and personal care products, they have not been applied effectively to provide improved deposition of benefit agents onto bleached hair.

Despite the prior art, there remains a need to deliver improved delivery of benefits to bleached hair.

We have now surprisingly found that compositions comprising a combination of defined branched surfactants in combination with a structurant and a fatty material provide an unexpectedly large enhancement in the deposition of conditioning benefit agents (eg silicones) onto bleached hair.

All percentages quoted herein are by weight based on total weight, unless otherwise stated.

DEFINITION OF THE INVENTION

Accordingly, there is provided a composition comprising:

(i) 0.01 to 10 wt % of a branched cationic conditioning surfactant; selected from Structure 1:

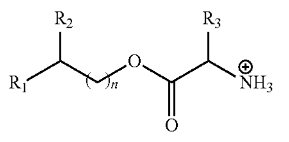

wherein:

$R_1$ and $R_2$ comprise linear alkyl chains, saturated or unsaturated, with carbon-carbon chain lengths of from $C_4$ to $C_{20}$, preferably from $C_6$ to $C_{18}$;

$R_3$ comprise either a proton or linear or branched alkyl chains, saturated or unsaturated, with carbon-carbon chain lengths of from $C_1$ to $C_5$; preferably from $C_1$ to $C_3$ n has a range of from 0 to 10, preferably selected from 0 and 1;

$X^{\ominus}$ is an organic or inorganic anion;

(ii) 0.1 to 10 wt % of a linear fatty material having at least one linear carbon-carbon chain, selected from a fatty alcohol, an alkoxylated fatty alcohol, a fatty acid and mixtures thereof;

(iii) 0.1 to 5 wt % of a structurant; and (iv) a particulate benefit agent selected from conditioning actives;

wherein the molar ratios of branched cationic conditioning surfactants (i) to linear fatty material (ii) are in the range of from 1:20 to 1:1, preferably from 1:10 to 1:1, most preferably 1:5 to 1:2.

In a second aspect, the invention provides a method of increasing deposition of a particulate benefit agent selected from conditioning actives, preferably silicone emulsion, to bleached hair comprising the step of applying to bleached hair a composition of the first aspect, compared with a similar composition that does not comprise a branched cationic conditioning surfactant in accordance with Structure 1, preferably compared with a composition that does not comprise branched cationic conditioning surfactants (i) and a linear fatty material (ii) in a molar ratio in the range of from 1:20 to 1:1, preferably from 1:10 to 1:1, most preferably 1:5 to 1:2.

The method of the invention preferably comprises an additional step of rinsing the composition from the bleached hair.

Preferably, the method is a method of increasing silicone deposition to bleached hair comprising the steps of applying to hair a composition as defined by the first aspect of the invention and rinsing the hair with water compared with a similar composition that does not comprise a branched cationic conditioning surfactant in accordance with Structure 1, preferably compared with a composition that does not comprise branched cationic conditioning surfactants (i) and a linear fatty material (ii) in a molar ratio in the range of from 1:20 to 1:1, preferably from 1:10 to 1:1, most preferably 1:5 to 1:2.

A third aspect provides a use of a composition of the first aspect to deliver increased amount of particulate benefit agent selected from conditioning actives, preferably silicones, to bleached hair, compared with a similar composition that does not comprise a branched cationic conditioning surfactant in accordance with Structure 1, preferably compared with a composition that does not comprise branched cationic conditioning surfactants (i) and a linear fatty material (ii) in a molar ratio in the range of from 1:20 to 1:1, preferably from 1:10 to 1:1, most preferably 1:5 to 1:2.

Compositions in accordance with the invention are preferably formulated as conditioners for the treatment of hair (typically after shampooing) and subsequent rinsing.

General Description of the Invention

Preferably, the treatment composition is selected from a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition, for example an oil treatment, and most preferably selected from a rinse-off hair conditioner, a hair mask and a leave-on conditioner composition. The treatment composition is preferably selected from a rinse-off hair conditioner and a leave-on conditioner.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes, and preferably are applied to the hair after washing and not rinsed out until the next wash.

The Branched Cationic Conditioning Surfactant

The branched cationic conditioning surfactant is present in an amount of from 0.01 to 10 wt %, preferably from 0.01 to 5 wt %, most preferably 0.1 to 2 wt % (at 100% active and based on weight of total composition).

The molar ratio of branched cationic conditioning surfactants (i) to linear fatty material (ii) is in the range of from 1:20 to 1:1, preferably from 1:10 to 1:1, most preferably 1:5 to 1:2.

The branched cationic conditioning surfactant contains an ester group is selected from structure 1.

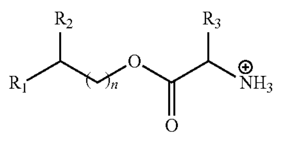

wherein:

- $R_1$ and $R_2$ comprise linear alkyl chains, saturated or unsaturated, with carbon-carbon chain lengths of from $C_4$ to $C_{20}$, preferably from $C_6$ to $C_{18}$;
- $R_3$ comprise either a proton or linear or branched alkyl chains, saturated or unsaturated, with carbon-carbon chain lengths of from $C_1$ to $C_5$; preferably from $C_1$ to $C_3$
- n has a range of from 0 to 10, preferably selected from 0 and 1; and
- $X^{\ominus}$ is an organic or inorganic anion;

wherein the molar ratios of branched cationic surfactants (i) to linear fatty material (ii) are in the range of from 1:20 to 1:1, preferably from 1:10 to 1:1, most preferably 1:5 to 1:2.

In structure 1, the amine head group is charged within the final formulation. Raw materials include, however, species where the charge is not permanent and can be induced by protonation in the formulation using a strong acid.

Optionally, at least one of $R_1$ and $R_2$, comprise linkages within the alkyl chain selected from the group consisting of an ester group (—OCO— or —COO—), an amido group (—NOC— or NCO—), and an ether group (—O—).

$X^{\ominus}$ is an organic or inorganic anion. Preferably, $X^{\ominus}$ comprises an anion selected from the halide ions; sulphates of the general formula $RSO_3^-$, wherein R is a saturated or unsaturated alkyl radical having 1 to 4 carbon atoms, and anionic radicals of organic acids.

Preferred halide ions are selected from fluoride, chloride, bromide and iodide. Preferred anionic radicals of organic acids are selected from maleate, fumarate, oxalate, tartrate, citrate, lactate and acetate. Preferred sulphates are methanesulphonate and ethanesulphonate.

Most preferably, $X^{\ominus}$ comprises an anion selected from a halide, a methanesulfonate group and an ethanesulphonate group.

In a preferred embodiment,

- $R_1$ and $R_2$ comprise linear alkyl chains, saturated or unsaturated, with carbon-carbon chain lengths of from $C_4$ to $C_{20}$, preferably from $C_6$ to $C_{18}$;
- $R_3$ comprise either a proton or linear or branched alkyl chains, saturated or unsaturated, with carbon-carbon chain lengths of from $C_1$ to $C_5$; preferably from $C_1$ to $C_3$
- n has a range of from 0 to 10, preferably selected from 0 and 1; and
- $X^{\ominus}$ is an organic or inorganic anion;

Methods for preparation of suitable branched cationic surfactants are known in the art and described, for example, in Chemistry, A European Journal, 2008, 14, 382. For example, 2-((2-octyldodecyl)oxy)-2-oxoethan-1-aminium methanesulphonate can be synthesized by the acid-catalysed condensation reaction of glycine with the specific guerbet alcohol, furnishing the desired product in one step.

Examples of suitable materials conforming to structure 1 are 2-((2-butyloctyl)oxy)-2-oxoethan-1-aminium methanesulphonate, 2-((2-hexyldecyl)oxy)-2-oxoethan-1-aminium methanesulphonate, 2-((2-octyldodecyl)oxy)-2-oxoethan-1-aminium methanesulphonate, 2-((2-decyltetradecyl)oxy)-2-oxoethan-1-aminium methanesulphonate, 2-((2-dodecylhexadecyl)oxy)-2-oxoethan-1-aminium methanesulphonate and 2-((2-tetradecyloctadecyl)oxy)-2-oxoethan-1-aminium methanesulphonate. Alternatively, a chloride counterion may be substituted for the methanesulphonate in the above examples.

The Fatty Material

The composition of the invention comprises from 0.1 to 10 wt % of a linear fatty material.

The combined use of fatty materials and cationic surfactants in conditioning compositions is believed to be especially advantageous, because this leads to the formation of a structured lamellar or liquid crystal phase, in which the cationic surfactant is dispersed.

Fatty materials comprise carbon-carbon chains. The term "linear" means that the carbon-carbon chains are linear in nature (ie free from branching). A "linear fatty material" has only linear carbon-carbon chains. The linear chains may be saturated or unsaturated.

The "linear fatty material" is selected from linear fatty alcohol, a linear alkoxylated fatty alcohol, a linear fatty acid and mixtures thereof. Preferably the linear fatty material is selected from a linear fatty alcohol and a linear fatty acid and mixtures thereof, most preferably a linear fatty alcohol.

Preferably, the alkyl chain of the fatty material is fully saturated. Representative fatty materials comprise from 8 to 22 carbon atoms, more preferably 16 to 22.

Suitable fatty alcohols comprise from 8 to 22 carbon atoms, preferably 16 to 22, most preferably C16 to C18. Fatty alcohols are typically compounds containing straight chain alkyl groups. Preferably, the alkyl groups are saturated. Examples of preferred fatty alcohols include cetyl alcohol, stearyl alcohol and mixtures thereof. The use of these materials is also advantageous in that they contribute to the overall conditioning properties of compositions for use in the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.1 to 10, and preferably from 0.1 to 5 percent by weight of the total composition.

The Structurant

The compositions of the invention comprise a structurant. The structurant is non-ionic.

The non-ionic structurant is preferably selected from unmodified structurants, hydrophobically modified structurants and mixtures thereof, most preferably unmodified.

Cationic structurants, such as phosphorylated starches, are not suitable because the positive charge competes with silicone to deposit on hair. Cationic structurants are materials that, whilst may be nonionic in salt form, dissociate in solution to form cationic species.

In the present invention, a nonionic structurant does not form a cationic species in solution.

Preferably, the structurant has a molecular weight ranging from 500 kDa to 2 MDa.

Preferably, the structurant is a polysaccharide, preferably derived from cellulose.

Examples of suitable structurants include Hydroxy Ethyl Cellulose (HEC) (a non-modified structurant) available, for example, under the tradename Natrosol™, in a range available from Ashland. Another suitable polysaccharide example is Structure XL (a non-modified starch), available from Nouryon. Another suitable cellulosic structurant is Plantasens Biogum Tara, available from Clariant.

Suitable hydrophobically modified structurants comprise both hydroxyethyl and long-chain alkyl groups. For example hydrophobically modified HEC, available as Natrosol Plus 330, or Polysurf™ 67 (ex Ashland).

The most preferred structurant is Hydroxy Ethyl Cellulose.

The Particulate Benefit Agent

The composition of the invention comprises a particulate benefit agent. The particulate benefit agent is selected from conditioning actives. Most preferably the particulate benefit agent is a silicone emulsion.

The total amount of particulate benefit agent is preferably from 0.1 wt % to 10 wt % of the total composition more preferably from 0.1 wt % to 5 wt %, even more preferably 0.25 wt % to 3 wt % and most preferably 0.25 to 1.5 wt %.

Preferred silicone emulsions do not comprise a hydrophobic modification, preferably the silicone emulsion is not a myristyloxyl modified silicone, most preferably not a myristyloxyl modified silicone or a cetyloxyl modified silicone. Most preferably, the silicone emulsions for use in the compositions of the invention are selected from emulsions of dimethicone, dimethiconol, amodimethicone and mixtures thereof.

Suitable emulsified silicones include polydimethylsiloxanes which have the CTFA designation dimethicone. Also suitable for use compositions of the invention are polydimethyl siloxanes having hydroxyl end groups, which have the CTFA designation dimethiconol. Preferably, the silicone is selected from the group consisting of dimethicone, dimethiconol, amodimethicone and mixtures thereof. Also preferred are blends of amino-functionalised silicones with dimethicones.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in compositions of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone". A preferred amodimethicone is commercially available from Dow Corning as DC 7134.

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

Optional Linear Cationic Conditioning Surfactant

Compositions may comprise a linear cationic conditioning surfactant, which is cosmetically acceptable and suitable for topical application to the hair.

Preferably, the linear cationic conditioning surfactants have the formula 1: $N^+(R^1)(R^2)(R^3)(R^4)$, wherein $R^1$, $R^2$, $R^3$ and $R^4$ are independently ($C_1$ to $C_{30}$) alkyl or benzyl.

In formula 1, preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—), amido (—NOC— or NCO—), and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable quaternary amine salts for use in conditioner compositions according to the invention are quaternary amine salt comprising from 12 to 24 carbon atoms, preferably from 16 to 22 carbon atoms.

Suitable quaternary amine salts for use in conditioner compositions according to the invention include cetyltrimethylammonium chloride, behenyltrimethylammonium chloride, Behentrimonium methosulphate, BehenylAmido Propyl Di-Methyl Amine, cetyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, Stearalkonium Chloride, Stearalkonium methosulphate, didodecyldimethylammonium chloride, dioctadecyldimethylammonium chloride, tallowtrimethylammonium chloride. dihydrogenated tallow dimethyl ammonium chloride (e.g., Arquad 2HT/75 from Akzo Nobel) and cocotrimethylammonium chloride.

Preferred quaternary amine salts selected from behenyltrimethylammonium chloride, Behentrimonium methosulphate, cetyltrimethylammonium chloride, and mixtures thereof.

A particularly useful cationic surfactant for use in conditioners according to the invention is cetyltrimethylammonium chloride, available commercially, for example as GENAMIN CTAC, ex Hoechst Celanese. Another particularly preferred cationic surfactant for use in conditioners according to the invention is behenyltrimethylammonium chloride, available commercially, for example as GENAMIN KDMP, ex Clariant.

Further suitable cationic surfactants include those materials having the CTFA designations Quaternium-5, Quaternium-31, and Quaternium-18. Mixtures of any of the foregoing materials may also be suitable.

Another example of a class of suitable cationic surfactants for use in the invention, either alone or together with one or more other cationic surfactants, is a combination of (i) and (ii) below:

(i) an amidoamine corresponding to the general formula (II):

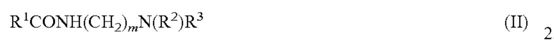

$R^1CONH(CH_2)_mN(R^2)R^3$ (II)

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine (TAS), stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethyl-amine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pennsylvania, USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton New Jersey, USA).

Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a (TAS) tertiary amine salt (stearamidopropyl dimethylamine) in situ in the hair treatment composition. The stearamidopropyl dimethylamine in effect is a non-permanent quaternary ammonium or pseudo-quaternary ammonium cationic surfactant.

Suitably, the acid is included in a sufficient amount to protonate more than 95 mole % (293 K) of the amidoamine present.

In conditioners for use in the invention, the level of linear cationic conditioning surfactant will generally range from 0.01 to 10%, more preferably 0.05 to 7.5%, most preferably 0.1 to 5% by total weight of cationic conditioning surfactant based on the total weight of the composition.

Further Ingredients

The composition according to the invention may comprise any of a number of ingredients which are common to hair conditioning compositions.

Other ingredients may include, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally, these optional ingredients are included individually at a level of up to about 5% by weight of the total composition.

Preferably, the further ingredients include perfumes, preservatives, colours and conditioning silicones.

The compositions of the invention are preferably free from viscosity modifiers and thickening agents for example thickening polymers.

Mixtures of any of the above active ingredients may also be used.

Generally, such ingredients are included individually at a level of up to 2%, preferably up to 1%, by weight of the total composition.

Embodiments of the invention are given in the following examples, in which all percentages are quoted by weight based on total weight unless otherwise stated.

EXAMPLES

Example 1: Composition 1 in Accordance with the Invention and Comparative Compositions A and B The following compositions were prepared:

Comparative Example A: comprises linear alkyl surfactant and does not contain a structurant Comparative Example B: contains a branched cationic (ester) surfactant, according to Structure 1, but no structurant Example 1: comprises a branched cationic (ester) surfactant, according to Structure 1, and a structurant.

TABLE 1

Compositions of Example 1 (in accordance with the invention) and Comparative Examples A and B.

| | | Inclusion level [wt %] | | |
|---|---|---|---|---|
| Ingredient | Trade/INCI name | A | B | 1 |
| Branched cationic surfactant | 2-((2-octyldodecyl)oxy)-2-oxoethan-1-aminium methanesulphonate | — | 1.85 | 1.85 |
| Linear alkyl surfactant | Genamin BTLF | 2.29 | — | — |
| Fatty alcohol | Ginol 1618 TA | 3.20 | 4.15 | 4.15 |
| Structurant | Natrosol 250 HHR PC | — | — | 1.00 |
| Fragrance | | 0.60 | 0.60 | 0.60 |
| Silicone | Xiameter MEM-7134 | 1.43 | 1.43 | 1.43 |
| Water | | To 100 | To 100 | To 100 |

Example 2: Treatment of Hair with Compositions A, B and 1

The hair (virgin) used was dark brown European hair, in switches of 5 g weight and 6 inches in length.

Bleaching of virgin hair was carried out using by applying Platine Precision White Compact Lightening Powder (L'Oreal Professionnel Paris, Paris, France) mixed with 9% cream peroxide, 30 'vol' (Excel GS Ltd, UK) (60 g of powder mixed with 120 g cream peroxide) and leaving for 30 minutes. Hair was then rinsed with water for 2 minutes.

Virgin or bleached hair was first treated with a cleansing shampoo using the following method:

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute.

The wet hair (virgin or bleached) was then treated with the compositions using the following method:

Conditioner was applied to the wet hair at a dose of 0.2 ml of conditioner per 1 g of hair and massaged into the hair for 1 minute. The hair was rinsed under running water for 1 minute and excess water removed.

Example 3: Silicone Deposition onto Bleached Hair Treated with Compositions A, B and 1 and Virgin Hair by A and 1

TABLE 2

Amount of silicone deposited on hair treated with Examples A and B (comparative) and Example 1 (in accordance with the invention).

| | Example | | |
|---|---|---|---|
| | A | B | 1 |
| Silicone deposition [ppm] - bleached hair | 229 | 183 | 949 |
| Silicone deposition st. dev. [ppm] - bleached hair | 14 | 28 | 58 |
| Silicone deposition [ppm] - Virgin Hair | 1102 | — | 1059 |
| Silicone deposition st. dev. [ppm] - Virgin Hair | 62 | — | 47 |

Comparative Example A is a typical composition representative of the prior art, containing linear alkyl surfactants. Comparative Example A deposits 1100 ppm silicone onto virgin hair, but if used on bleached hair, its deposition is only 230 ppm. This is illustrative of the problem solved by the present invention.

Comparative Example B, outside the scope of the present invention, incorporates the branched cationic surfactant but lacks the structurant. Consequently, lower deposition performance is achieved.

The composition of the present invention, represented by Example 1, differs from the Comparative Examples A and B in that it contains both a branched cationic material and a structurant material. It will be seen that a dramatic increase in the amount of silicone is achieved. Further, the deposition onto virgin is maintained.

The invention claimed is:

1. A composition comprising:

(i) 0.01 to 10 wt % of a branched cationic conditioning surfactant; selected from structure 1,

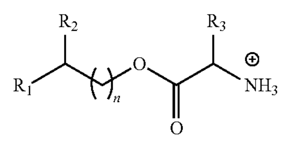

and an organic or inorganic ion $X^-$, wherein:

$R_1$ and $R_2$ comprise linear alkyl chains, saturated or unsaturated, with carbon-carbon chain lengths of from $C_4$ to $C_{20}$;

$R_3$ comprise either a proton or linear or branched alkyl chains, saturated or unsaturated, with carbon-carbon chain lengths of from $C_1$ to $C_5$;

n has a range of from 0 to 10;

(ii) 0.1 to 10 wt % of a linear fatty material comprising linear carbon-carbon chains, selected from a fatty alcohol, an alkoxylated fatty alcohol, a fatty acid and mixtures thereof;

(iii) 0.1 to 5 wt % of a nonionic structurant; and (iv) a particulate benefit agent selected from conditioning actives;

wherein the molar ratio of branched cationic surfactants (i) to linear fatty material (ii) is in the range of from 1:20 to 1:1.

2. The composition of claim 1, wherein the structurant is a nonionic polysaccharide.

3. The composition of claim 2, wherein the structurant is hydroxyethyl cellulose.

4. The composition of claim 1, wherein the conditioning actives are silicone emulsions.

5. The composition of claim 4, wherein the silicone emulsions are selected from emulsions of dimethicone, dimethiconol, amodimethicone and mixtures thereof.

6. The composition of claim 4, wherein the silicone emulsions are not myristyloxyl modified silicone.

7. The composition of claim 1, wherein the particulate benefit agent is present in an amount of from 0.1 wt % to 10 wt % of the total composition.

8. The composition of claim 7, wherein the particulate benefit agent is present in an amount of from 0.25 to 1.5 wt %.

9. The composition of claim 1, wherein $X^-$ comprises an anion selected from a halide, a methanesulfonate group and an ethanesulphonate group.

10. The composition of claim 1, wherein the molar ratio of branched cationic surfactants (i) to linear fatty material (ii) is in the range of from 1:10 to 1:1.

11. The composition of claim 1, wherein the branched cationic conditioning surfactant is present in an amount of from 0.01 to 5 wt %.

12. A method of increasing deposition of a particulate benefit agent selected from conditioning actives, scalp actives, encapsulated fragrance, emulsified fragrance, and mixtures thereof to bleached hair, the method comprising the steps of applying to hair a composition of claim 1 and rinsing the hair with water, wherein deposition of the particulate benefit agent is increased compared with a composition similar to the composition of claim 1 but that does not comprise a branched cationic conditioning surfactant in accordance with Structure 1.

13. The method of claim 12 wherein the particulate benefit agent is selected from conditioning actives.

14. The method of claim 13, wherein the particulate benefit agent is a silicone emulsion.

15. The composition of claim 6, wherein the silicone emulsions are not a myristyloxyl modified silicone or a cetyloxyl modified silicone.

* * * * *